(12) United States Patent
Katsumoto et al.

(10) Patent No.: US 10,989,722 B2
(45) Date of Patent: *Apr. 27, 2021

(54) ELECTRICAL MEASURING CONTAINER, ELECTRICAL MEASURING APPARATUS AND ELECTRICAL MEASURING METHOD

(71) Applicant: SONY CORPORATION, Tokyo (JP)

(72) Inventors: Yoichi Katsumoto, Tokyo (JP); Marcaurele Brun, Tokyo (JP); Yoshihito Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/566,039

(22) Filed: Sep. 10, 2019

(65) Prior Publication Data

US 2020/0003793 A1 Jan. 2, 2020

Related U.S. Application Data

(63) Continuation of application No. 14/095,657, filed on Dec. 3, 2013, now Pat. No. 10,466,257.

(30) Foreign Application Priority Data

Dec. 12, 2012 (JP) .................. 2012-271612

(51) Int. Cl.
*G01N 33/86* (2006.01)
*G01N 33/49* (2006.01)
(Continued)

(52) U.S. Cl.
CPC ......... *G01N 33/86* (2013.01); *G01N 33/4905* (2013.01); *G01N 27/02* (2013.01)

(58) Field of Classification Search
None
See application file for complete search history.

(56) References Cited

U.S. PATENT DOCUMENTS 3,840,806 A * 10/1974 Stoner .................. G01N 27/07
324/722
4,319,194 A * 3/1982 Cardinal ............... G01N 33/86
324/449
(Continued)

FOREIGN PATENT DOCUMENTS

CN 1357300 A 7/2002
CN 102308203 A 1/2012
(Continued)

OTHER PUBLICATIONS

Office Action for CN Patent Application No. 201711103781.7, dated Jul. 31, 2019, 12 pages of Office Action and 14 pages of English Translation.

(Continued)

*Primary Examiner* — Jill A Warden
*Assistant Examiner* — Brittany I Fisher
(74) *Attorney, Agent, or Firm* — Chip Law Group (57) ABSTRACT

There is provided an electrical measuring container of a biological sample in a liquid phase, including at least a biological sample holding section that accommodates a biological sample in a liquid phase and made of a resin, and an electrical conductive section fixed to the biological sample holding section. In a state in which a portion of the electrical conductive section is buried in the biological sample holding section, the biological sample holding section and the electrical conductive section are integrally formed with each other.

16 Claims, 9 Drawing Sheets

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
33: HOLDING SECTION
34: BENDING SECTION
S: BIOLOGICAL SAMPLE (51) Int. Cl.
*G01N 27/02* (2006.01)
*G01R 27/26* (2006.01)

(56) References Cited

U.S. PATENT DOCUMENTS

| | | | |
|---|---|---|---|
| 5,495,176 A | 2/1996 | Shiranita et al. | |
| 5,837,199 A * | 11/1998 | Dumschat | G01N 27/283 422/68.1 |
| 8,008,063 B2 * | 8/2011 | Ragsdale | C12N 13/00 204/403.01 |
| 2003/0011386 A1 * | 1/2003 | Xie et al. | G01N 33/2823 324/694 |
| 2004/0072357 A1 * | 4/2004 | Stiene | A61B 5/14514 324/449 |
| 2006/0016701 A1 | 1/2006 | Qin et al. | |
| 2007/0140902 A1 * | 6/2007 | Calatzis | G01N 27/07 422/400 |
| 2010/0099094 A1 * | 4/2010 | Okada | C12Q 1/682 435/6.16 |
| 2011/0309848 A1 * | 12/2011 | Eberheim | B22F 3/225 324/724 |
| 2014/0162348 A1 * | 6/2014 | Katsumoto | G01N 33/86 435/287.1 |

FOREIGN PATENT DOCUMENTS

| | | |
|---|---|---|
| CN | 102435855 A | 5/2012 |
| CN | 102465094 A | 5/2012 |
| JP | 55-050162 A | 4/1980 |
| JP | 58-022946 A | 2/1983 |
| JP | 58-171655 A | 10/1983 |
| JP | 61-017942 A | 1/1986 |
| JP | 07-311136 A | 11/1995 |
| JP | 2004-522146 A | 7/2004 |
| JP | 2005-077148 A | 3/2005 |
| JP | 2007-003414 A | 1/2007 |
| JP | 2007-304116 A | 11/2007 |
| JP | 2009-042141 A | 2/2009 |
| JP | 2010-181400 A | 8/2010 |
| JP | 2012-052906 A | 3/2012 |
| JP | 2012-518156 A | 8/2012 |
| WO | 91/009295 A1 | 6/1991 |

OTHER PUBLICATIONS

Office Action for JP Patent Application No. 2018-173691, dated Aug. 20, 2019, 03 pages of Office Action and 02 pages of English Translation.
Non-Final Office Action for U.S. Appl. No. 14/095,657, dated Aug. 11, 2016, 11 pages.
Non-Final Office Action for U.S. Appl. No. 14/095,657, dated Sep. 22, 2017, 16 pages.
Non-Final Office Action for U.S. Appl. No. 14/095,657, dated Jan. 25, 2019, 13 pages.
Final Office Action for U.S. Appl. No. 14/095,657, dated Mar. 15, 2017, 14 pages.
Final Office Action for U.S. Appl. No. 14/095,657, dated Apr. 6, 2018, 14 pages.
Advisory Action for U.S. Appl. No. 14/095,657, dated Jul. 14, 2017, 05 pages.
Advisory Action for U.S. Appl. No. 14/095,657, dated Jul. 26, 2018, 04 pages.
Notice of Allowance for U.S. Appl. No. 14/095,657, dated Jun. 4, 2019, 07 pages.
Office Action for JP Patent Application No. 2017-000489, dated Oct. 31, 2017, 05 pages of Office Action and 33 pages of English Translation.
Office Action for JP Patent Application No. 2018-173691, dated Apr. 7, 2020, 05 pages of Office Action and 04 pages of English Translation.

* cited by examiner

FIG. 1

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

FIG. 3

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
33: HOLDING SECTION
S: BIOLOGICAL SAMPLE
M: MAGNET

FIG. 8

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
33: HOLDING SECTION
34: BENDING SECTION
S: BIOLOGICAL SAMPLE

FIG. 9

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
33: HOLDING SECTION
34: BENDING SECTION
S: BIOLOGICAL SAMPLE
10: ELECTRICAL MEASURING APPARATUS
4: APPLICATION UNIT
5: MEASUREMENT UNIT
6: ANALYSIS UNIT

ELECTRICAL MEASURING CONTAINER, ELECTRICAL MEASURING APPARATUS AND ELECTRICAL MEASURING METHOD

CROSS REFERENCE TO RELATED APPLICATIONS

The present application is a continuation application of U.S. patent application Ser. No. 14/095,657, filed Dec. 3, 2013, which claims priority from prior Japanese Priority Patent Application JP 2012-271612 filed Dec. 12, 2012, the entire contents of which are incorporated herein by reference.

BACKGROUND

The present technology relates to an electrical measuring container configured to measure electrical properties of a biological sample in a liquid phase, and more particularly, an electrical measuring container having a structure configured to precisely measure electrical properties of a biological sample in a liquid phase and enabling easy industrial production, and an electrical measuring apparatus and an electrical measuring method using the electrical measuring container.

Measurement of electrical properties of a biological sample in a liquid phase, determination of physical properties of the sample from the measurement current result, and discrimination of a kind of cell or the like included in the sample, and so on, are performed (for example, see Japanese Patent Application Laid-open No. 2009-042141). The measured electrical properties may be complex permittivity or frequency dispersion (a dielectric spectrum) thereof. The complex permittivity or the frequency dispersion is generally calculated by measuring a complex capacitance and complex impedance between electrodes using a solution retainer or the like including the electrodes configured to apply a voltage to a solution.

In addition, for example, in Japanese Patent Application Laid-open No. 2010-181400, a technology of obtaining information related to blood coagulation from permittivity of blood is disclosed, and "a blood coagulation system analysis device including a pair of electrodes, an application unit configured to apply an alternating current voltage to the pair of electrodes at predetermined time intervals, a measurement unit configured to measure the permittivity of the blood disposed between the pair of electrodes, and an analysis unit configured to analyze a level of function of the blood coagulation system using the permittivity of the blood measured at the time intervals after an action of the anticoagulant agent functioned in the blood is released" is disclosed.

When the electrical properties of the biological sample of the liquid phase are measured, as a container configured to accommodate the biological sample, for example, Japanese Patent Application Laid-open No. 2012-052906 discloses a sample cartridge having a cylindrical body made of an insulating material, configured to hold the liquid sample in a region including surfaces of electrodes inserted into an inner hole from both of end openings and a surface of the inner hole, and in which a constriction section disposed between the two opposite electrodes and formed by constricting the inner hole is installed at that region, measuring electrical properties of a liquid sample.

Here, in order to measure the electrical properties of the biological sample in the liquid phase, a measuring electrode should come in contact with the biological sample in the liquid phase. In the related art, measurement is performed in a state in which the biological sample in the liquid phase is accommodated in the container to which the measuring electrode is adhered and fixed. However, in this method, for example, when the electrical properties of the blood as a biological sample are measured, coagulation activity of the blood may be accelerated according to the kind of used adhesive agent, and may exert an influence on objective measurement.

In addition, even when an adhesive agent having low coagulability is temporarily used, since manufacturing processes for manufacturing the container are increased, productivity may be degraded.

Meanwhile, as a method not using the adhesive agent, for example, a method of measuring electrical properties in a state in which electrodes are inserted from the outside into a container configured to accommodate a biological sample is performed. However, in this method, a measurement error may occur due to a difference in insertion amount of the electrodes into the liquid sample.

In addition, since configurations of external apparatuses are increased, the apparatus is increased in size, the manufacturing process is complicated, and the apparatus is increased in price.

SUMMARY

As described above, when electrical measurement of the liquid sample is performed using the container to which the electrodes are previously adhered and fixed, the adhesive agent may exert an influence on a biological body material or productivity may be decreased. Meanwhile, in measurement using external electrodes, a measurement error may occur, the manufacturing process may be complicated, and the apparatus may be increased in price.

Here, it is desirable to provide an electrical measuring container including a structure configured to precisely measure electrical properties of a biological sample in a liquid phase and enabling industrial production.

The inventors of the application have diligently researched a structure of a container used when a biological sample in a liquid phase is measured, and devised a method of forming the container by focusing on not using the gluing agent, completing the present technology.

That is, in the present technology, first, there is provided an electrical measuring container of a biological sample in a liquid phase, which includes at least: a biological sample holding section configured to accommodate the biological sample in the liquid phase and made of a resin; and an electrical conductive section fixed to the biological sample holding section, wherein, in a state in which a portion of the electrical conductive section is buried in the biological sample holding section, the biological sample holding section and the electrical conductive section are integrally formed with each other.

In the electrical measuring container according to the present technology, since the electrical conductive section and the biological sample holding section are integrally formed with each other in a state in which the portion of the electrical conductive section is buried in the biological sample holding section, the electrical conductive section may be fixed to the biological sample holding section without using a gluing agent.

While a specific method of the integral forming is not particularly limited, for example, as the electrical conductive section is insert-formed in the biological sample holding section, the electrical conductive section and the biological sample holding section may be integrally formed with each other.

In the electrical measuring container according to the present technology, the electrical conductive section may include at least an electrode section in contact with the biological sample upon measurement, and a connecting section configured to be electrically connected to an external circuit.

While the electrode section of the electrical conductive section may be freely disposed according to a purpose of measurement, for example, one or more pairs of electrode sections may be provided.

In addition, the electrode section may also be disposed to be included in a portion of an inner wall of the electrical measuring container. In this case, in the inner wall, a connecting section of the biological sample holding section and the electrode section may be smoothly configured.

Further, the electrode section may also be disposed to be positioned a predetermined distance above a portion that becomes a bottom section upon measurement.

In the electrical measuring container according to the present technology, at least a portion of the electrical conductive section may function as a holding section configured such that the electrical conductive section is disposed at a predetermined place of the biological sample holding section upon the integral forming.

The biological sample configured to measure electrical properties using the electrical measuring container according to the present technology may be, for example, a biological sample containing a sedimentary ingredient. More specifically, for example, a biological sample containing a blood ingredient may be provided.

When the electrical measuring container according to the present technology is used for the electrical measurement of the biological sample containing the sedimentary ingredient, the electrode section may be disposed to be positioned above a position at which an accumulation sedimentation fraction of the sedimentary ingredient from the portion that becomes the bottom section upon measurement is equal to or larger than a volume fraction.

In the electrical measuring container according to the present technology, a bending section may be installed at the portion buried in a biological sample holding section of the electrical conductive section.

While the kind of resin used in the electrical measuring container according to the present technology is not particularly limited, for example, one or more kinds of resins selected from polypropylene, polystyrene, acryl and polysulfone may be used.

In addition, in the electrical measuring container according to the present technology, while a material having electrical conductivity used in the electrical conductive section is not particularly limited, for example, an electrically conductive material containing titanium may be used.

While the electrical measuring container according to the present technology may be used in all of the electrical measurements, for example, the electrical measuring container may be used to measure permittivity of the biological sample of impedance of the biological sample.

More specifically, when the biological sample including the blood ingredient is used, in order to measure a blood sedimentation situation or a blood coagulation situation, the electrical measuring container according to the present technology may be used.

The electrical measuring container according to the present technology may be appropriately used as a portion of an electrical measuring apparatus.

Specifically, there is provided an electrical measuring apparatus of a biological sample in a liquid phase, which includes at least: a biological sample holding section configured to accommodate the biological sample in the liquid phase and made of a resin;

an electrical conductive section, at least a portion of which comes in contact with the biological sample upon measurement;

an application unit configured to apply a voltage to the electrical conductive section; and a measurement unit configured to measure electrical properties of the biological sample, wherein, in a state in which a portion of the electrical conductive section is buried in the biological sample holding section, the biological sample holding section and the electrical conductive section are integrally formed with each other.

In addition, the electrical measuring container according to the present technology may be appropriately used in an electrical measuring method of a biological sample in a liquid phase.

According to one or more of embodiments of the electrical measuring container of the present technology, the electrical conductive section is fixed to the biological sample holding section without using an adhesive agent. For this reason, the electrical properties of the biological sample in the liquid phase can be precisely measured without being influenced by an adhesive agent. In addition, since the electrical measuring container according to the present technology can be easily manufactured, the electrical measuring container can be produced at a low cost in large quantities.

DETAILED DESCRIPTION OF THE EMBODIMENTS

Hereinafter, preferred modes for carrying out the present technology will be described in detail with reference to the appended drawings. In addition, the embodiments to be described below are representative exemplary embodiments of the present technology, and thus, the scope of the present technology is not interpreted narrowly. Further, the description will be provided in the following sequence.

1. Electrical Measuring Container 1
(1) Biological Sample Holding Section 2
(2) Electrical Conductive Section 3
(a) Electrode Section 31
<First Embodiment>
<Second Embodiment>
<Third Embodiment>
<Fourth Embodiment>
(b) Connecting Section 32
(c) Holding Section 33
<Fifth Embodiment>
(d) Bending Section 34
<Sixth Embodiment>
(3) Biological Sample S
(4) Others
2. Electrical Measuring Apparatus 10
(1) Application Unit 4
(2) Measurement Unit 5
(3) Analysis Unit 6
3. Electrical Measuring Method
1. Electrical Measuring Container 1

Figure 1:
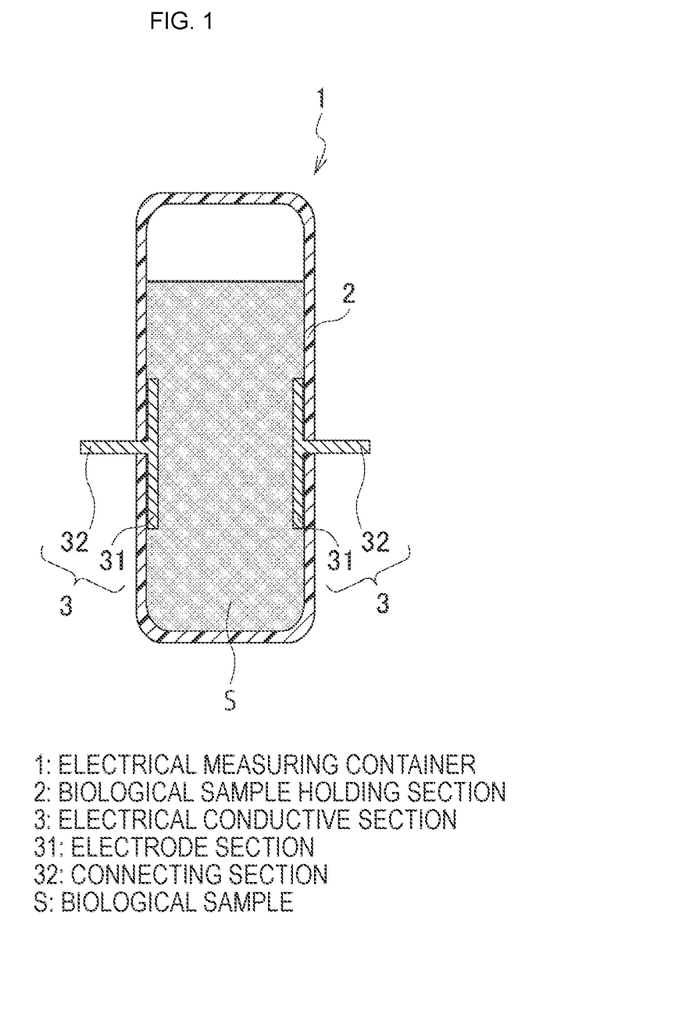
FIG. 1 is a schematic cross-sectional view schematically showing a first embodiment of an electrical measuring container 1 according to the present technology.

FIG. 1 is a schematic cross-sectional view schematically showing a first embodiment of an electrical measuring container 1 according to the present technology. The electrical measuring container 1 according to the present technology is a container used to hold a biological sample in a liquid phase when electrical properties of the biological sample are measured. The electrical measuring container 1 according to the present technology generally includes at least a biological sample holding section 2 and an electrical measuring container conductive section 3. Hereinafter, the respective parts will be described in detail. In addition, in the respective drawings, for the purpose of the description, while a biological sample S is shown, the biological sample S is not included in the electrical measuring container 1 according to the present technology.

(1) Biological Sample Holding Section 2

The biological sample holding section 2 is an area in which a liquid phase biological sample of a measurement target is held. In the electrical measuring container 1 according to the present technology, the biological sample holding section 2 is characterized to be made of a resin.

In the electrical measuring container 1 according to the present technology, the kind of resin used in the biological sample holding section 2 is not particularly limited, and one or two or more kinds of resins that can be appropriately applied to the biological sample in the liquid phase may be freely selected and used. For example, a hydrophobic and insulating polymer such as polypropylene, polymethyl methacrylate, polystyrene, acryl, polysulfone, polytetrafluoroethylene, or the like, a copolymer, a blend polymer or the like may be used. In the present technology, in the above-mentioned polymers, in particular, the biological sample holding section 2 may be made of one or more kinds of resins selected from polypropylene, polystyrene, acryl, and polysulfone. Since these resins have a property such as a low coagulation activity with respect to the blood, for example, the container can be appropriately used for measurement of the biological sample containing the blood.

In the electrical measuring container 1 according to the present technology, a specific shape of the biological sample holding section 2 is not particularly limited, and a cylindrical body, a polygonal cylindrical body having a polygonal (triangular, rectangular, etc.) cross-section, a circular conical body, a polygonal conical body having a polygonal (triangular, rectangular, etc.) cross-section, or a combined shape of one or two or more cross-sections, may be freely designed according to the kind of biological sample S, a measuring method, a used measurement, or the like, as long as the biological sample S in the liquid phase can be held.

In a state in which the biological sample S in the liquid phase is held in the biological sample holding section 2, measurement of various kinds of electrical properties is performed. For this reason, the biological sample holding section 2 may be configured to be sealable in a state in which the biological sample S is held. However, a time to measure the various kinds of electrical properties of the biological sample S in the liquid phase may be delayed, and the section may not be configured to be hermetically sealed as long as the measurement is not influenced.

A specific introducing and sealing method of the biological sample S in the liquid phase to the biological sample holding section 2 is not particularly limited and the biological sample S can be freely introduced according to the shape of the biological sample holding section 2. For example, while not shown, a method of installing a lid section at the biological sample holding section 2, introducing the biological sample S using a pipette or the like, and then closing and sealing the lid section, or a method of inserting an injection needle from an outer surface of a biological sample holding section, injecting the biological sample S in the liquid phase, and then closing and sealing an area penetrated by the injection needle with grease or the like, may be provided.

(2) Electrical Conductive Section 3

In the electrical measuring container 1 according to the present technology, the electrical conductive section 3 is characterized in that it is previously fixed to the biological sample holding section 2. In particular, in the present technology, in a state in which a portion of the electrical conductive section 3 is buried in the biological sample holding section 2, the biological sample holding section 2 and the electrical conductive section 3 are configured to be integrally formed with each other. That is, no fixing material such as an adhesive agent or the like is used in fixing of the biological sample holding section 2 and the electrical conductive section 3.

When the fixing is performed using an adhesive agent, properties of the biological sample S may be influenced according to the kind of adhesive agent used. For example, when electrical properties of the blood as the biological sample S are measured, coagulation activity of the blood may be accelerated according to the kind of adhesive agent used, and may exert an influence on the desired measurement. However, in the electrical measuring container 1 according to the present technology, since the adhesive agent is not used to fix the biological sample holding section 2 and the electrical conductive section 3, the influence on the biological sample S by the adhesive agent can be excluded. As a result, the electrical properties of the biological sample S can be precisely measured.

In addition, even when an adhesive agent having a small influence on the biological sample S is temporarily used, since an adhering process is increased due to the adhesive agent when the container is manufactured, productivity may be degraded. However, in the manufacturing process of the electrical measuring container 1 according to the present technology, since the biological sample holding section 2 and the electrical conductive section 3 are integrally formed with each other, the adhering does not have to be separately provided in addition to the forming process of the biological sample holding section 2. As a result, the electrical measuring container 1 can be easily manufactured, and the electrical measuring container 1 can be produced at a low cost in large quantities.

Meanwhile, as the method using no adhesive agent, for example, a method of measuring electrical properties in a state in which electrodes are inserted from the outside into a container configured to accommodate a biological sample is provided. In this method, a measurement error may occur due to a difference in insertion amount of the electrodes into the liquid sample. However, in the electrical measuring container 1 according to the present technology, the electrical conductive section 3 is previously fixed to the biological sample holding section 2. For this reason, as will be described below, as the electrical conductive section 3 is used as the electrode, the measurement error due to the difference in insertion amount of the electrodes into the liquid sample can be removed. As a result, the electrical properties of the biological sample S can be precisely measured.

In addition, as the electrical conductive section 3 is previously fixed to the biological sample holding section 2, a relative positioning mechanism or the like between the electrode and the container may not be installed at the side of the apparatus, and the apparatus may be simply configured. As a result, this contributes to realization of miniaturization of the apparatus, simplification of the manufacturing process, a low cost of the apparatus, and the like.

Further, since the number of parts of the electrical measuring container 1 can be reduced, user convenience can also be improved.

A specific method of integrally forming the biological sample holding section 2 and the electrical conductive section 3 is not particularly limited, and in a state in which a portion of the electrical conductive section 3 is buried in the biological sample holding section 2, as long as the biological sample holding section 2 and the electrical conductive section 3 can be fixed without using an adhesive agent, a free method can be used. For example, when the resin forming the biological sample holding section 2 is solidified from a melted state, as the electrical conductive section 3 is disposed at a predetermined position, the biological sample holding section 2 and the electrical conductive section 3 can be integrally formed with each other. As a more specific method, for example, the biological sample holding section 2 and the electrical conductive section 3 can be integrally formed by inserting the electrical conductive section 3 into a mold and injecting the resin around the electrical conductive section 3 to integrate the electrical conductive section 3 and the resin, which is known as insert molding.

In this way, in the electrical measuring container 1 according to the present technology, when the biological sample holding section 2 is formed, since the electrical conductive section 3 is simultaneously fixed, the manufacturing process can be simplified. As a result, the electrical measuring container 1 can be produced at a low cost in large quantities.

The electrical conductive section 3 is made of a material having electrical conductivity. In the electrical measuring container 1 according to the present technology, the kind of material having electrical conductivity used in the electrical conductive section 3 is not particularly limited, and one or two or more kinds of materials that can be appropriately applied to electrical measurement of the biological sample S in the liquid phase can be freely selected and used. For example, titanium, aluminum, stainless steel, platinum, gold, copper, graphite, or the like may be used. In the present technology, among the materials, in particular, the electrical conductive section 3 may be made of a material having electrical conductivity and including titanium. Since titanium has a property such as a low coagulation activity with respect to the blood, for example, titanium can be appropriately used for measurement of the biological sample containing the blood.

The electrical conductive section 3 includes an electrode section 31 and a connecting section 32. In addition, according to necessity, a holding section 33 and a bending section 34 may be further provided. Hereinafter, the respective parts will be described in detail.

(a) Electrode Section 31

The electrode section 31 comes in contact with the biological sample S upon measurement to be used to apply a voltage desired for the biological sample S. In the electrical measuring container 1 according to the present technology, the number of electrode sections 31 may be freely designed according to a desired electrical measuring method or the like. For example, when permittivity or impedance of the biological sample S is measured, one or more pairs of electrode sections 31 may be installed.

In addition, when a disposition, shape or the like of the electrode section 31 is not particularly limited and the voltage for the biological sample S can be applied, the electrode section 31 can be freely designed according to the desired electrical measuring method or the like. Hereinafter, an example of disposition of the electrode section 31 will be disposed in detail.

First Embodiment

The first embodiment shown in FIG. 1 is an example in which the pair of electrode sections 31 are disposed along an inner wall of the biological sample holding section 2. More specifically, for example, in a state in which a portion of the electrical conductive section 3 is buried in a sidewall of the biological sample holding section 2, the electrode section 31 is disposed inside the biological sample holding section 2 and the connecting section 32 (to be described below) is disposed outside the biological sample holding section 2. The electrode section 31 is disposed in vicinity of a center of the sidewall of the biological sample holding section 2.

Second Embodiment

Figure 2A:
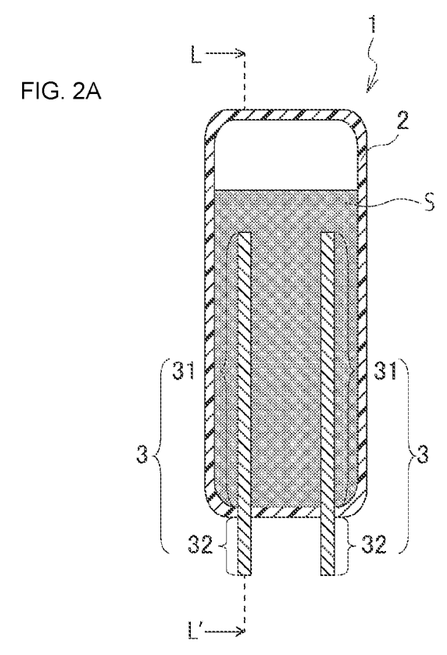
FIG. 2A is a schematic cross-sectional view schematically showing a second embodiment of the electrical measuring container 1 according to the present technology.
Figure 2B:
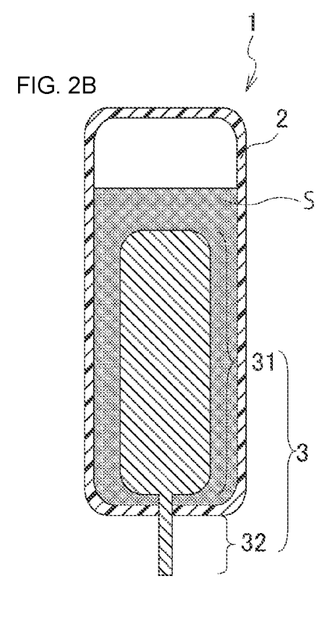
FIG. 2B is a cross-sectional view taken along line L-L' of FIG. 2A.

FIG. 2A is a schematic cross-sectional view schematically showing a second embodiment of the electrical measuring container 1 according to the present technology, and FIG. 2B is a cross-sectional view taken along line L-L' of FIG. 2A. The second embodiment is an example in which the pair of electrical conductive sections 3 are disposed in a state protruding from a bottom wall section of the biological sample holding section 2. More specifically, for example, in a state in which a portion of the electrical conductive section 3 is buried in the bottom wall section of the biological sample holding section 2, the electrode section 31 is disposed inside the biological sample holding section 2 and the connecting section 32 (to be described below) is disposed outside the biological sample holding section 2.

In the embodiment, a shape of the electrode section 31 is not particularly limited, and the electrode section 31 can be freely designed according to the shape of the biological sample holding section 2 or a desired electrical measuring method. In the present disclosure, in particular, in order to improve measurement efficiency, the electrode section 31 may come in surface contact with the liquid sample. As a specific shape, as shown in FIG. 2B, as a portion of the electrode section 31 in contact with the liquid sample is increased, the electrode section 31 can come in surface contact with the liquid sample.

Third Embodiment

Figure 3:
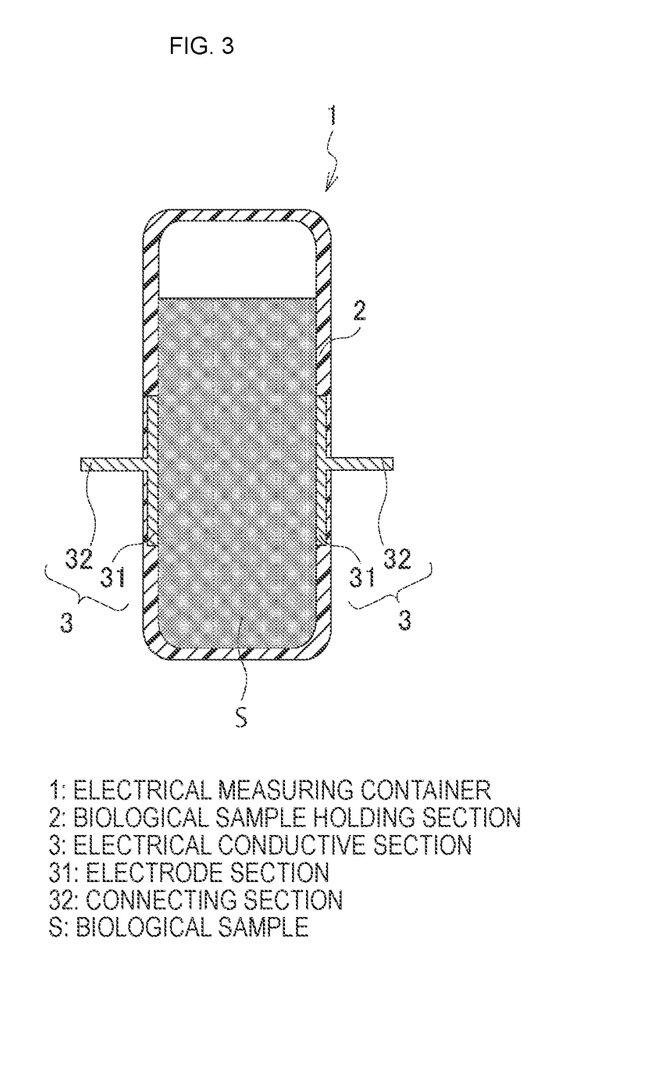
FIG. 3 is a schematic cross-sectional view schematically showing a third embodiment of the electrical measuring container 1 according to the present technology.

FIG. 3 is a schematic cross-sectional view schematically showing a third embodiment of the electrical measuring container 1 according to the present technology. The third embodiment is an example in which the pair of electrode sections 31 is included in a portion of the inner wall of the electrical measuring container 1. More specifically, for example, in a state in which a portion of the electrode section 31 is buried in a sidewall of the biological sample holding section 2, the electrode section 31 is disposed as a portion of the inner wall of the electrical measuring container 1 and the connecting section 32 (to be described below) is disposed outside the biological sample holding section 2.

In this way, when the electrode section 31 is disposed to be included in a portion of the inner wall of the electrical measuring container 1, as described in the third embodiment shown in FIG. 3, a connecting section of the biological sample holding section 2 and the electrode section 31 may be smoothly and integrally formed. In the case of the biological sample S in the liquid phase, when a step difference occurs in the container, bubbles or the like may remain therein, which may influence the measurement value. However, as the container is configured not to generate a step difference or the like at a boundary between the biological sample holding section 2 and the electrode section 31, retention of bubbles or the like can be prevented, and as a result, the electrical properties of the biological sample S can be more precisely measured.

In addition, when the one or more pairs of electrode sections 31 are provided, the electrode sections 31 may be disposed in parallel while measuring the electrical properties of the biological sample S. However, for example, in consideration of release characteristics or the like when the insert molding or the like is performed, the respective electrode sections 31 can be disposed in a state in which several inclinations are provided.

Fourth Embodiment

Figure 4A:
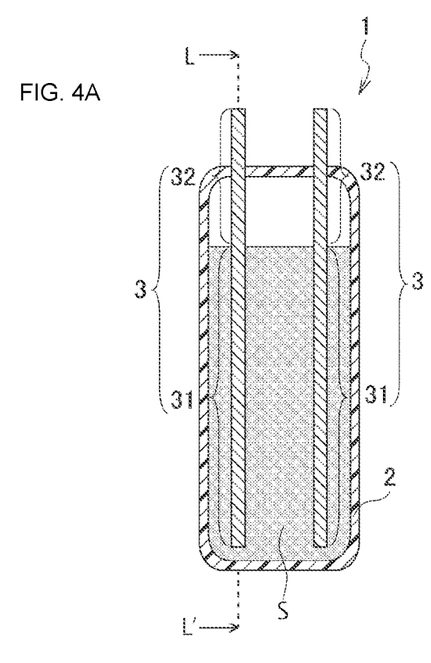
FIG. 4A is a schematic cross-sectional view schematically showing a fourth embodiment of the electrical measuring container 1 according to the present technology.
Figure 4B:
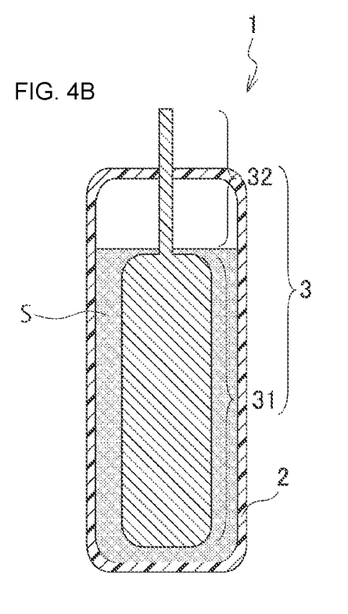
FIG. 4B is a cross-sectional view taken along line L-L' of FIG. 4A.

FIG. 4A is a schematic cross-sectional view schematically showing a fourth embodiment of the electrical measuring container 1 according to an embodiment of the present technology, and FIG. 4B is a cross-sectional view taken along line L-L' of FIG. 4A. The fourth embodiment is an example in which the pair of electrical conductive sections 3 are disposed to protrude from an upper wall section of the biological sample holding section 2. More specifically, for example, in a state in which a portion of the electrical conductive section 3 is buried in the upper wall section of the biological sample holding section 2, the electrode section 31 is disposed inside the biological sample holding section 2 and the connecting section 32 (to be described below) is disposed outside the biological sample holding section 2. As the electrical conductive section 3 protrudes from the upper wall section of the biological sample holding section 2, for example, in comparison with the embodiment in which the electrical conductive section 3 protrudes from the bottom wall section as described in the above-mentioned second embodiment, leakage of the sample can be more reliably prevented.

In the embodiment, a shape of the electrode section 31 is not particularly limited, and the electrode section 31 may be freely designed according to a shape of the biological sample holding section 2 or a desired electrical measuring method. For example, similar to the above-mentioned second embodiment, as a portion of the electrode section 31 in contact with the liquid sample is increased (see FIG. 4B), when the electrode section 31 is designed to come in surface contact with the liquid sample, measurement efficiency can be improved.

The electrical measuring container 1 according to the first, third or fourth embodiment is characterized in that the electrode section 31 is disposed a predetermined distance above a portion that becomes a bottom section upon measurement. For example, as will be described below, when the biological sample containing the sedimentary ingredient is used as the biological sample S, as the electrode section 31 is disposed a predetermined distance above the portion that becomes the bottom section upon measurement, a time-elapsed influence on the sedimentary ingredient due to the sedimentation can be suppressed. As a result, the electrical properties of the biological sample S can be more precisely measured.

Figure 5A:
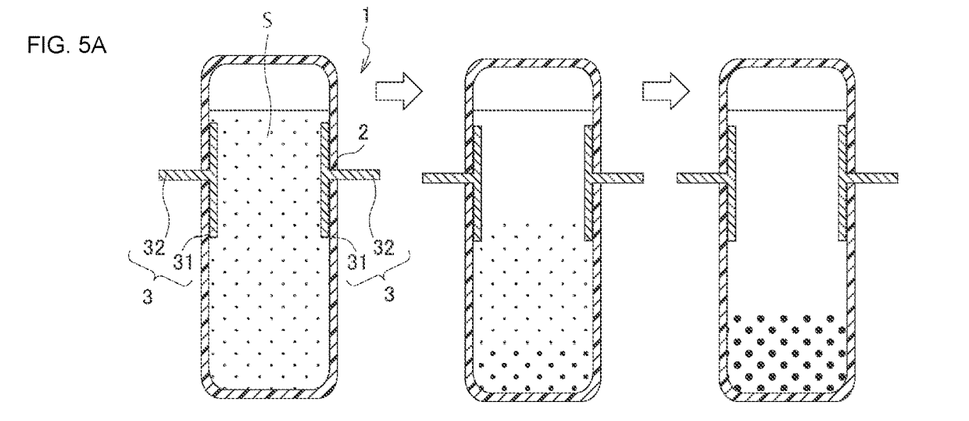
FIGS. 5A, 5B, and 5C are schematic cross-sectional views schematically showing a relation between an aspect of time-elapsed sedimentation of a sedimentary ingredient and a position of an electrode section 31 when a biological sample S containing a sedimentary ingredient is used.
Figure 5B:
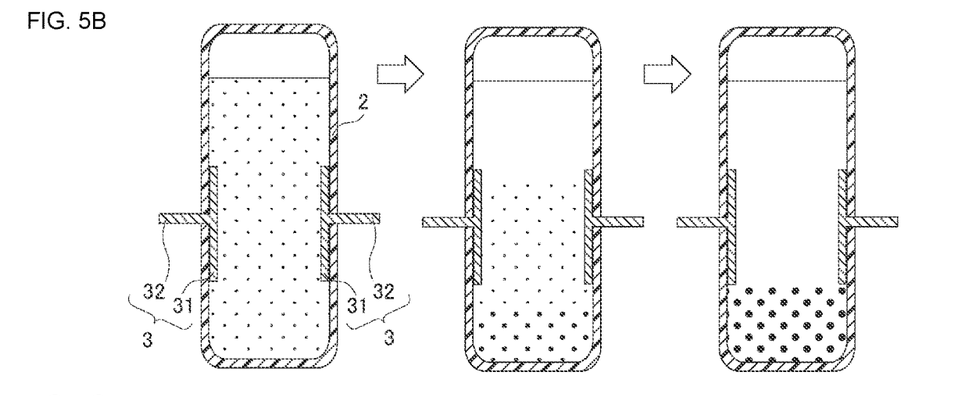
Figure 5C:
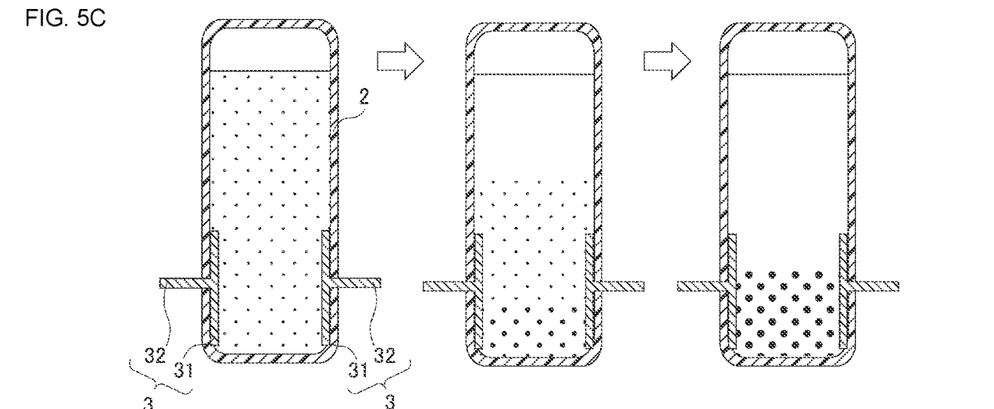
Figure 6:
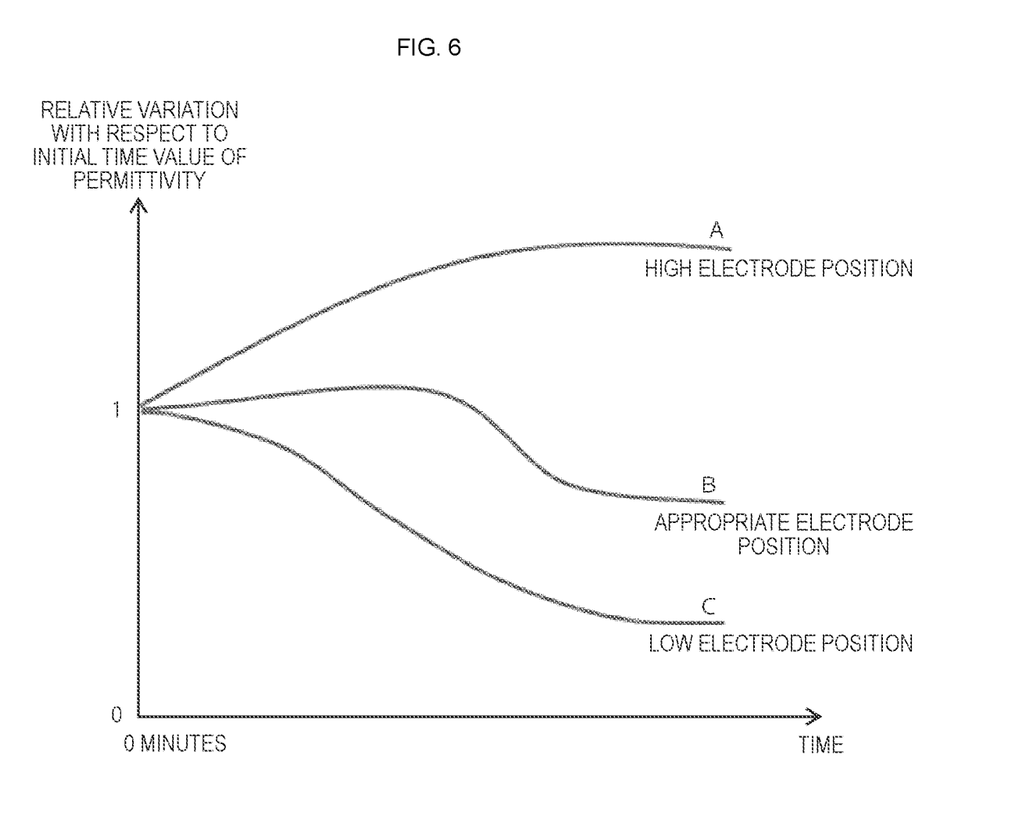
FIG. 6 is a graph showing an example of a relation between the position of the electrode section 31 corresponding to FIGS. 5A, 5B, and 5C and a measurement value when permittivity is measured.

Appropriate positioning of the electrode section 31 when the biological sample S containing the sedimentary ingredient is used will be described with reference to FIGS. 5A, 5B, 5C, and 6. FIGS. 5A, 5B, and 5C are schematic cross-sectional views schematically showing a relation between an aspect of time-elapsed sedimentation of the sedimentary ingredient and a position of the electrode section 31 when the biological sample S containing the sedimentary ingredient is used. FIG. 6 is a graph showing an example of a relation between the position of the electrode section 31 corresponding to FIGS. 5A, 5B, and 5C and a measurement value when permittivity is measured.

For example, as shown in FIG. 5B, when the electrode section 31 is disposed to be positioned a predetermined distance above the portion that becomes the bottom section upon measurement, as shown in FIG. 6B, a certain interval from the measurement shows a certain permittivity. As shown in FIG. 5B, this is because, even with the time-elapsed sedimentation of the sedimentary ingredient, a concentration of the sedimentary ingredient in a region narrowed at the pair of electrode sections 3 does not substantially vary up to a certain time.

Meanwhile, as shown in FIG. 5A, when the electrode section 31 is disposed at a high position, as shown in FIG. 6A, permittivity is increased immediately after the measurement starts. This is because, as shown in FIG. 5A, the concentration of the sedimentary ingredient in the region narrowed at the pair of electrode sections 31 is reduced by advance of the sedimentation of the sedimentary ingredient immediately after the measurement starts.

In addition, as shown in FIG. 5C, when the electrode section 31 is disposed at a low position, as shown in FIG.

6C, permittivity is lowered immediately after the measurement starts. This is because, as shown in FIG. 5C, the concentration of the sedimentary ingredient in the region narrowed at the pair of electrode sections 31 is increased by advance of the sedimentation of the sedimentary ingredient immediately after the measurement starts.

In this way, as shown in FIG. 5B, as the electrode section 31 is disposed a predetermined distance above the portion that becomes the bottom section upon measurement, even when the sedimentation of the sedimentary ingredient progresses in the biological sample S, precise measurement can be performed without influencing the measurement value in the middle of the sedimentation (see FIG. 6B). As a more specific position, the electrode section 31 may be disposed to be positioned above a position at which an accumulation sedimentation fraction of the sedimentary ingredient from the portion that becomes the bottom section upon measurement is equal to or larger than a volume fraction. When disposed at such a position, precise measurement can be performed for a longer time.

In addition, a relative variation of permittivity of a graph of FIG. 6 merely shows an example, and the variation may differ according to the kind of the biological sample S of the measurement target.

As an example of the biological sample S containing the sedimentary ingredient, the case in which whole blood is used as a measurement target will be described. In the case of a healthy adult human, the whole blood includes red blood cells of a volume fraction of about 40%. The red blood cells are deposited under a settling condition, and finally precipitated at a lower portion of the container. Meanwhile, serums are mainly collected on an upper layer section. During progress of the sedimentation process, three layers of a red blood cell precipitation layer, a whole blood layer and a serum layer are generally provided from a lower side thereof.

When the whole blood is used as the measurement target, the electrode section 31 may be disposed such that the measurement of the whole blood is performed for a long time as much as possible. Specifically, most lines of electric force emitted from the electrode section 31 and passing through a target sample may be disposed to continuously pass through the whole blood layer while avoiding the red blood cell precipitation layer and the serum layer sequentially generated in the container. As a specific disposition satisfying this, the electrode section 31 may be disposed such that a lower limit of the electrode section 31 is disposed above a position at which an accumulated volume fraction from the lower side is equal to or larger than a red blood cell volume fraction. In addition, the electrode section 31 may be disposed such that an upper limit of the electrode section 31 is disposed under the lower limit of the serum layer when a minimal time for the measurement elapses.

(b) Connecting Section 32

The connecting section 32 is an area electrically connected to an external circuit. A specific shape of the connecting section 32 is not particularly limited, and the connecting section 32 can be designed in a free shape as long as the connecting section comes in electrical contact with the external circuit.

(c) Holding Section 33

Fifth Embodiment

Figure 7A:
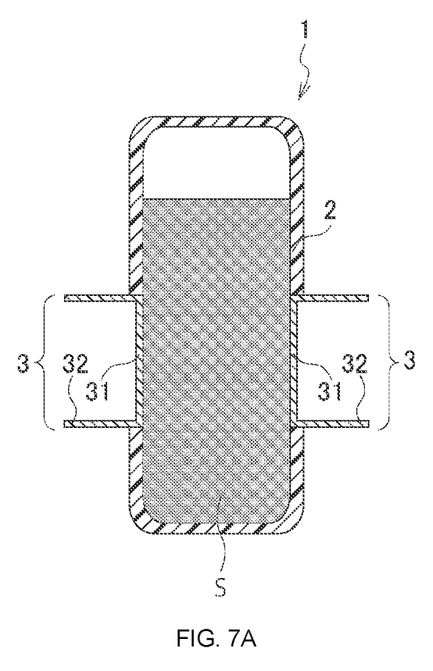
FIGS. 7A and 7B are schematic cross-sectional views schematically showing a fifth embodiment of the electrical measuring container 1 according to the present technology.
Figure 7B:
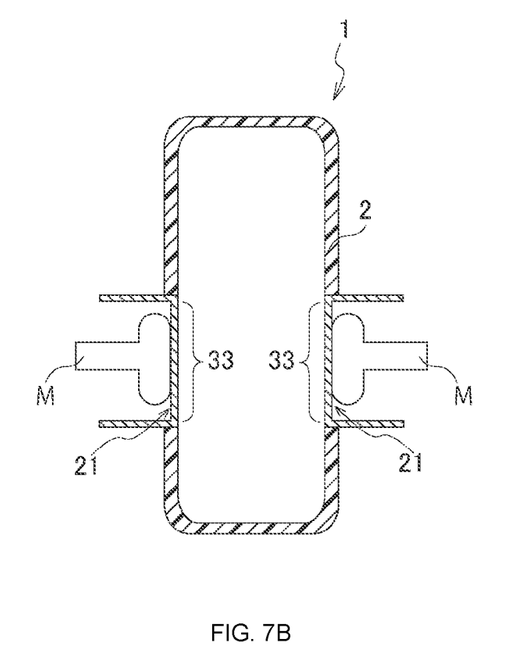

FIGS. 7A and 7B are schematic cross-sectional views schematically showing a fifth embodiment of the electrical measuring container 1 according to an embodiment of the present technology. The fifth embodiment is a configuration that does not include a resin at a portion of the pair of electrode sections 31 outside the container. According to the above-mentioned configuration, for example, upon formation of the biological sample holding section 2, as the electrical conductive section 3 is positioned and fixed using, for example, a magnet M or the like, the electrical conductive section 3 (in particular, the electrode section 31) can be positioned at a desired position of the electrical measuring container 1 (see FIG. 7B).

In addition, a fixing unit from the outside of the container is not limited to the magnet M shown in FIG. 7B, and any unit may be used as long as the fixing unit can fix the electrical conductive section 3 from the outside of the container.

In this way, as at least a portion of the electrical conductive section 3 functions as the holding section 33 such that the electrical conductive section 3 is disposed at a predetermined place of the biological sample holding section 2 upon integral forming, the electrical measuring container 1 in which the electrical conductive section 3 is positioned at a desired place can be easily manufactured.

In addition, upon formation of the biological sample holding section 2, as the electrical conductive section 3 is held, deformation of the electrical conductive section 3 upon integral forming can be prevented.

Further, in the fifth embodiment shown in FIGS. 7A and 7B, while the electrode section 31 is configured to simultaneously function as the holding section 33, the present technology is not limited thereto. For example, the connecting section 32 may also be designed to simultaneously function as the holding section 33.

(d) Bending Section 34

Sixth Embodiment

Figure 8:
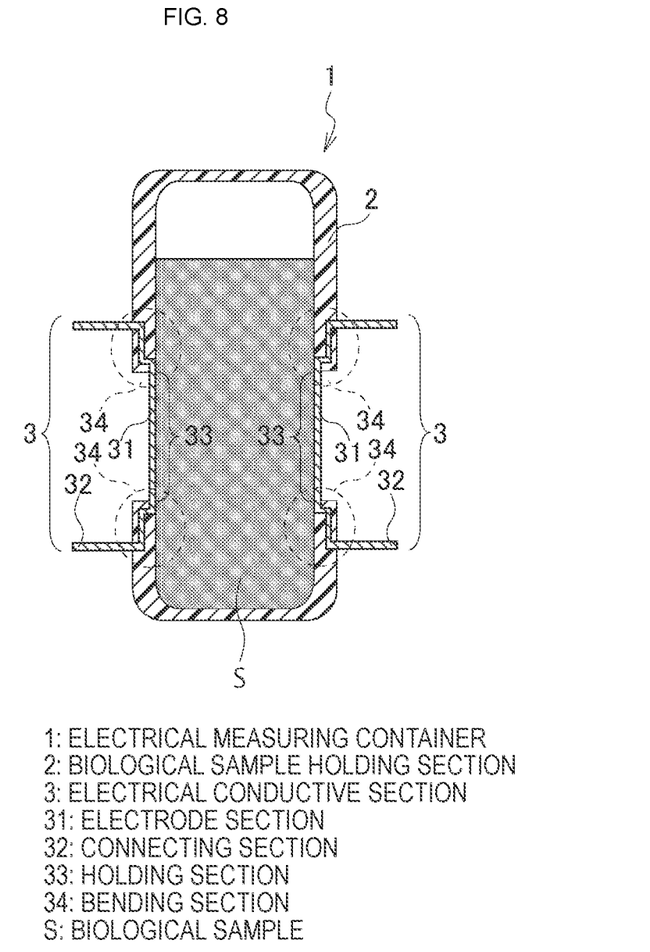
FIG. 8 is a schematic cross-sectional view schematically showing a sixth embodiment of the electrical measuring container 1 according to the present technology.

FIG. 8 is a schematic cross-sectional view schematically showing a sixth embodiment of the electrical measuring container 1 according to an embodiment of the present technology. The sixth embodiment is characterized in that the bending section 34 is provided at a portion of the electrical conductive section 3 buried in the biological sample holding section 2.

Since the electrical measuring container 1 according to an embodiment of the present technology is characterized in that the biological sample holding section 2 and the electrical conductive section 3 are integrally formed without using an adhesive agent or the like, leakage of the biological sample S in the liquid phase from a boundary between the biological sample holding section 2 and the electrical conductive section 3 is extremely rare. However, according to storage conditions or measurement conditions such as a temperature or the like due to a difference in distortion between the resin and the electrical conductive material or the like, leakage of the biological sample S in the liquid phase from the boundary between the biological sample holding section 2 and the electrical conductive section 3 may occur. Here, like the sixth embodiment shown in FIG. 8, as the bending section 34 is provided at the portion buried in the biological sample holding section 2 of the electrical conductive section 3, for example, in comparison with the fifth embodiment (see FIGS. 7A and 7B) that does not include the bending section 34, leakage of the biological sample S from the boundary between the biological sample holding section 2 and the electrical conductive section 3 can be prevented.

In addition, as the bending section 34 is provided at the portion buried in the biological sample holding section 2 of the electrical conductive section 3, since the biological sample holding section 2 and the electrical conductive section 3 are more strongly fixed, the electrical measuring container 1 can have a stronger structure.

(3) Biological Sample S

The biological sample S that can be used as the measurement target in the present technology is not particularly limited as long as the sample is in a liquid phase, and may be freely selected. For example, the biological sample S containing a sedimentary ingredient or the like may be provided. More specifically, the biological sample S containing blood ingredients such as whole blood, blood plasma, a diluted solution thereof, and/or drug additives, or the like, may be provided.

(4) Others

A predetermined drug may also be previously input into the electrical measuring container 1 according to an embodiment of the present technology. For example, when the biological sample S containing the blood ingredient is used as a measurement target, an anticoagulant agent, a coagulation initiator, or the like, may be previously input into the biological sample holding section 2 of the electrical measuring container 1.

The electrical measuring container 1 according to an embodiment of the present technology can be produced at a low cost in large quantities as described above. Using these characteristics, for example, the electrical measuring container 1 according to an embodiment of the present technology may be a disposable cartridge. As the disposable cartridge is used as the electrical measuring container 1 according to an embodiment of the present technology, effort of cleaning the container or the like can be reduced, and the measurement can be efficiently performed. In addition, generation of a measurement error or the like due to a separate biological sample S remaining in the container can be prevented, and the electrical properties of the biological sample S can be more precisely measured.

2. Electrical Measuring Apparatus 10

Figure 9:
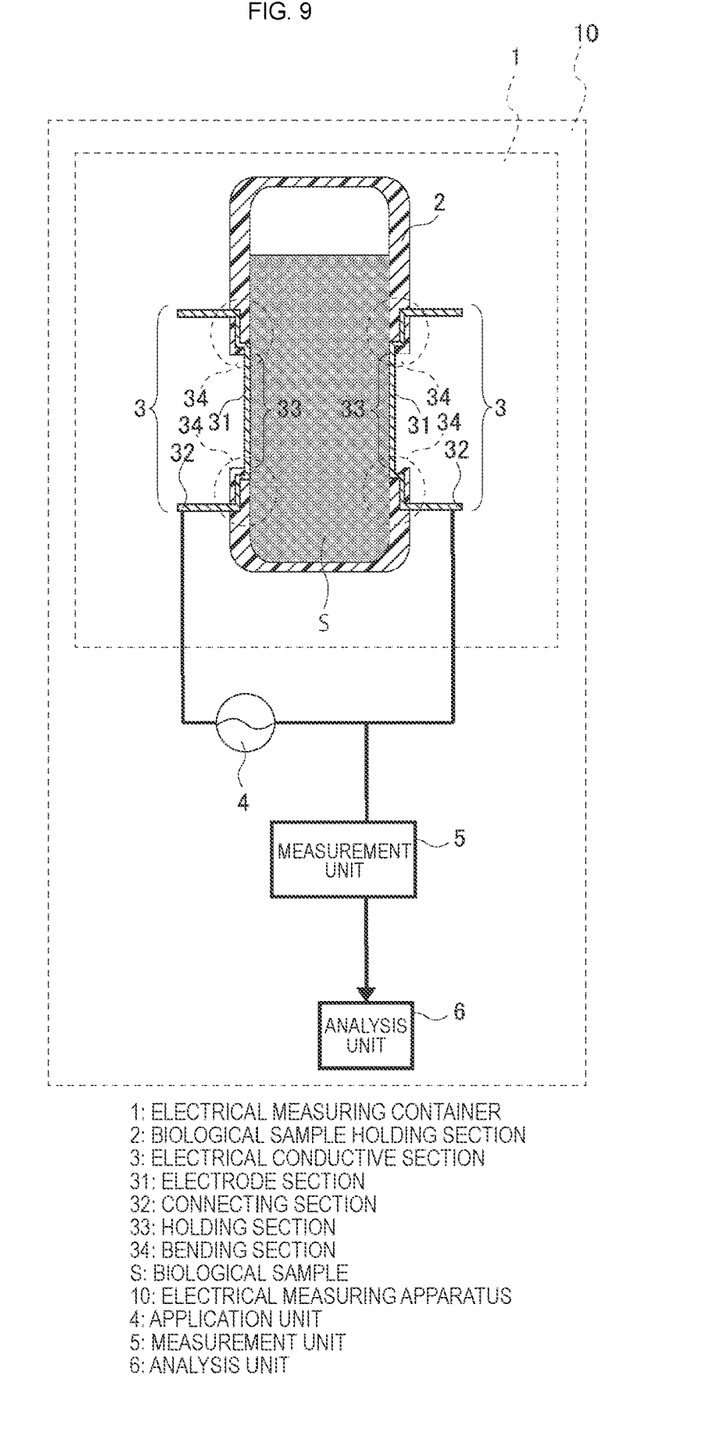
FIG. 9 is a schematic view schematically showing a first embodiment of an electrical measuring apparatus 10 according to the present technology.

FIG. 9 is a schematic view schematically showing the first embodiment of an electrical measuring apparatus 10 according to an embodiment of the present technology. In the embodiment, the electrical measuring container 1 according to the above-mentioned sixth embodiment is used. The electrical measuring apparatus 10 according to an embodiment of the present technology generally includes at least the above-mentioned electrical measuring container 1, an application unit 4 and a measurement unit 5. In addition, according to necessity, an analysis unit 6 may further provided. Hereinafter, the respective parts will be described in detail. In addition, since the electrical measuring container 1 is similar to that described above, the description thereof will be omitted.

(1) Application Unit 4

The application unit 4 applies a voltage to the electrical conductive section 3 of the electrical measuring container 1 according to an embodiment of the present technology. The application unit 4 applies a voltage to the electrical conductive section 3 of the electrical measuring container 1 when an order to initiate measurement is received or when power of the electrical measuring apparatus 10 is input as a start point. More specifically, the application unit 4 applies an alternating current voltage having a predetermined frequency to the electrical conductive section 3 at a set measurement interval. In addition, the voltage applied by the application unit 4 may be a direct current voltage according to the measured electrical properties.

(2) Measurement Unit 5

The measurement unit 5 measures electrical properties of the biological sample S in the liquid phase held in the electrical measuring container 1 according to an embodiment of the present technology. Specifically, electrical properties such as complex permittivity (hereinafter simply referred to as "permittivity"), frequency dispersion thereof, or the like, are measured when an order to initiate measurement is received or when power of the electrical measuring apparatus 10 is input. More specifically, for example, when the permittivity is measured, the measurement unit 5 measures a current or impedance between the electrode sections 31 of the electrical measuring container 1 at a predetermined period, and derives permittivity from the measured value. In deriving the permittivity, a known function or relational expression showing a relation between the current or impedance and the permittivity may be used.

(3) Analysis Unit 6

The analysis unit 6 receives electrical property data of the biological sample S derived from the measurement unit 5, and performs determination or the like of physical properties of the biological sample S. In the electrical measuring apparatus 10 according to an embodiment of the present technology, the analysis unit 6 may be omitted, and for example, the measurement unit 5 may perform analysis from the measured electrical property data using an external computer or the like.

Specifically, the electrical property data of the biological sample S derived from the measurement unit 5 is provided to the analysis unit 6 at measurement intervals, and the analysis unit 6 receives the electrical property data provided from the measurement unit 5 and starts determination or the like of the physical properties of the liquid sample. The analysis unit 6 informs of a result of the determination or the like of the physical properties of the liquid sample and/or permittivity data. The information may be converted into, for example, a graph to be displayed on a monitor or printed on a predetermined medium.

3. Electrical Measuring Method

The electrical measuring container 1 according to an embodiment of the present technology may be appropriately used to measure the electrical properties of the biological sample S in the liquid phase. The electrical properties that can be measured through an electrical measuring method according to an embodiment of the present technology are not particularly limited but may be freely measured according to the kind of the biological sample S, which is the measurement target, or physical properties to be analyzed. For example, permittivity, impedance, or the like, can be measured.

Using the electrical measuring method according to an embodiment of the present technology, for example, when the blood is used as the measurement target, a blood coagulation situation or a blood sedimentation situation can be analyzed from the measurement value of the permittivity or impedance. More specifically, for example, a parameter showing characteristics from a plurality of permittivity and/or impedance measurement values received during the analysis period can be derived, and the blood coagulation situation or the blood sedimentation situation can be analyzed based on comparison of the parameter with a reference value that determines a reference of acceleration of blood coagulability or progress of a blood sedimentation process. Additionally, the present technology may also be configured as below.

(1) An electrical measuring container of a biological sample in a liquid phase, including at least:
  a biological sample holding section configured to accommodate a biological sample in a liquid phase and made of a resin; and
  an electrical conductive section fixed to the biological sample holding section,
    wherein, in a state in which a portion of the electrical conductive section is buried in the biological sample holding section, the biological sample holding section and the electrical conductive section are integrally formed with each other.

(2) The electrical measuring container according to (1), wherein the electrical conductive section is integrated with the biological sample holding section through insert molding.

(3) The electrical measuring container according to (1) or (2),
  wherein the electrical conductive section includes at least
    an electrode section configured to come into contact with the biological sample upon measurement, and
    a connecting section configured to be electrically connected to an external circuit.

(4) The electrical measuring container according to (3), further including:
  one or more pairs of the electrode sections.

(5) The electrical measuring container according to (3) or (4), wherein the electrode section is included in a portion of an inner wall of the electrical measuring container.

(6) The electrical measuring container according to (5), wherein a connecting section of the biological sample holding section and the electrode section is smoothly formed at the inner wall.

(7) The electrical measuring container according to any one of (3) to (6), wherein the electrode section is disposed a predetermined distance above a portion that becomes a bottom section upon measurement.

(8) The electrical measuring container according to any one of (1) to (7), wherein at least a portion of the electrical conductive section functions as a holding section configured in a manner that the electrical conductive section is disposed at a predetermined place of the biological sample holding section when the biological sample holding section and the electrical conductive section are integrally formed with each other.

(9) The electrical measuring container according to any one of (1) to (8), wherein the biological sample contains a sedimentary ingredient.

(10) The electrical measuring container according to any one of (1) to (9), wherein the biological sample contains a blood ingredient.

(11) The electrical measuring container according to (9),
  wherein biological sample contains the sedimentary ingredient, and
  wherein the electrode section is disposed such that an accumulation sedimentation fraction of the sedimentary ingredient from the portion that becomes the bottom section upon measurement is disposed over a position at which the accumulation sedimentation fraction is equal to or larger than a volume fraction of the sedimentary ingredient.

(12) The electrical measuring container according to any one of (1) to (11), further including:
  a bending section at a portion of the electrical conductive section, the portion being buried in the biological sample holding section.

(13) The electrical measuring container according to any one of (1) to (12), wherein the resin includes one or more kinds of resins selected from polypropylene, polystyrene, acryl, and polysulfone.

(14) The electrical measuring container according to any one of (1) to (13), wherein the electrical conductive section is made of an electrical conductive material including titanium.

(15) The electrical measuring container according to any one of (1) to (14), wherein the electrical measuring container is used to measure permittivity of the biological sample.

(16) The electrical measuring container according to any one of (1) to (15), wherein the electrical measuring container is used to measure impedance of the biological sample.

(17) The electrical measuring container according to (10), wherein the electrical measuring container is used to measure a blood sedimentation situation.

(18) The electrical measuring container according to (10) or (17), wherein the electrical measuring container is used to measure a blood coagulation situation.

(19) An electrical measuring apparatus of a biological sample in a liquid phase, including at least:
  a biological sample holding section configured to accommodate a biological sample in a liquid phase and made of a resin;
  an electrical conductive section, at least a portion of the electrical conductive section being configured to come into contact with the biological sample upon measurement;
  an application unit configured to apply a voltage to the electrical conductive section; and
  a measurement unit configured to measure an electrical property of the biological sample,
    wherein, in a state in which a portion of the electrical conductive section is buried in the biological sample holding section, the biological sample holding section and the electrical conductive section are integrally formed with each other.

(20) An electrical measuring method of a biological sample in a liquid phase used to measure an electrical property of the biological sample using an electrical measuring container of the biological sample in the liquid phase, the electrical measuring container including at least
  a biological sample holding section configured to accommodate a biological sample in a liquid phase and made of a resin, and
  an electrical conductive section fixed to the biological sample holding section,
    wherein, in a state in which a portion of the electrical conductive section is buried in the biological sample holding section, the biological sample holding section and the electrical conductive section are integrally formed with each other.

Since the electrical measuring container 1 according to the present technology uses no adhesive agent to fix the biological sample holding section 2 and the electrical conductive section 3, an influence on the biological sample S due to the adhesive agent can be excluded. As a result, the electrical properties of the biological sample S can be precisely measured.

In addition, in the manufacturing process of the electrical measuring container 1 according to the present technology, since the biological sample holding section 2 and the electrical conductive section 3 are integrally formed with each other, the adhering process does not have to be separately provided in addition to the forming process of the biological sample holding section 2. As a result, the electrical measuring container 1 can be easily manufactured, and the electrical measuring container 1 can be produced at a low cost in large quantities.

Further, in the electrical measuring container 1 according to the present technology, the electrical conductive section 3 is previously fixed to the biological sample holding section 2. For this reason, as the electrical conductive section 3 is used as the electrode, a measurement error due to a difference in insertion amount of the electrodes into the liquid sample can be removed. As a result, the electrical properties of the biological sample S can be precisely measured.

In addition, as the electrical conductive section 3 is previously fixed to the biological sample holding section 2, the apparatus can be simply configured, and this can contribute to realization of miniaturization of the apparatus or simplification of the manufacturing process, a low cost of the apparatus, and so on.

It should be understood by those skilled in the art that various modifications, combinations, sub-combinations and alterations may occur depending on design requirements and other factors insofar as they are within the scope of the appended claims or the equivalents thereof.

What is claimed is:

1. An electrical measuring container, comprising:
   a biological sample holding section configured to accommodate a biological sample in a liquid phase, wherein the biological sample holding section comprises a resin;
   an electrical conductive section coupled with the biological sample holding section, wherein
      the biological sample holding section is integrally formed with the electrical conductive section based on a state in which a portion of the electrical conductive section is buried in the biological sample holding section, and
      the electrical conductive section comprises:
         an electrode section configured to come into contact with the biological sample upon measurement, wherein
            the electrode section is in a portion of an inner wall of the electrical measuring container, and
            a connecting section of the biological sample holding section and the electrode section is smoothly formed at the inner wall; and
         a connecting section configured to be electrically connected to an external circuit; and
      a bending section at the portion of the electrical conductive section.

2. The electrical measuring container according to claim 1, wherein the electrical conductive section is integrated with the biological sample holding section through insert molding.

3. The electrical measuring container according to claim 1, further comprising:
   a plurality of pairs of the electrode section.

4. The electrical measuring container according to claim 3, wherein the electrode section is at a distance above a portion of the biological sample holding section that becomes a bottom section of the biological sample holding section upon the measurement.

5. The electrical measuring container according to claim 1, wherein the portion of the electrical conductive section, as a holding section, is configured in a manner that the electrical conductive section is at a position of the biological sample holding section.

6. The electrical measuring container according to claim 1, wherein the biological sample comprises a sedimentary ingredient.

7. The electrical measuring container according to claim 6, wherein the electrode section is above a position at which an accumulation sedimentation fraction of the sedimentary ingredient from a portion of the biological sample holding section that becomes a bottom section of the biological sample holding section upon the measurement is equal to or larger than a volume fraction.

8. The electrical measuring container according to claim 1, wherein the biological sample comprises a blood ingredient.

9. The electrical measuring container according to claim 8, wherein the electrical measuring container is configured to measure a blood sedimentation situation.

10. The electrical measuring container according to claim 8, wherein the electrical measuring container is configured to measure a blood coagulation situation.

11. The electrical measuring container according to claim 1, wherein the resin includes a plurality of kinds of resins selected from polypropylene, polystyrene, acryl, and polysulfone.

12. The electrical measuring container according to claim 1, wherein
    the electrical conductive section further comprises an electrical conductive material, and
    the electrical conductive material includes titanium.

13. The electrical measuring container according to claim 1, wherein the electrical measuring container comprises a measurement section configured to measure permittivity of the biological sample.

14. The electrical measuring container according to claim 1, wherein the electrical measuring container comprises a measurement section configured to measure impedance of the biological sample.

15. The electrical measuring container according to claim 1, wherein the biological sample is a whole blood.

16. An electrical measuring apparatus, comprising:
    a biological sample holding section configured to accommodate a biological sample in a liquid phase, wherein the biological sample holding section comprises a resin;
    an electrical conductive section, wherein the electrical conductive section comprises:
       an electrode section configured to come into contact with the biological sample upon measurement, wherein
          the electrode section is in a portion of an inner wall of the electrical measuring apparatus, and
          a connecting section of the biological sample holding section and the electrode section is smoothly formed at the inner wall; and
       a connecting section configured to be electrically connected to an external circuit;
    an application unit configured to apply a voltage to the electrical conductive section; and
    a measurement unit configured to measure an electrical property of the biological sample, wherein
       the biological sample holding section is integrally formed with the electrical conductive section based on a state in which the portion of the electrical conductive section is buried in the biological sample holding section; and
    a bending section at the portion of the electrical conductive section, wherein
       the biological sample is a whole blood.

* * * * *